United States Patent

Stewart et al.

[11] Patent Number: 5,525,411
[45] Date of Patent: Jun. 11, 1996

[54] UPHOLSTERY FABRIC WITH ELECTRICALLY CONDUCTIVE BACKING

[75] Inventors: William H. Stewart, Campobello; Roy P. DeMott, Spartanburg, both of S.C.

[73] Assignee: Milliken Research Corporation, Spartanburg, S.C.

[21] Appl. No.: 217,668

[22] Filed: Mar. 25, 1994

[51] Int. Cl.⁶ .................................................. B32B 5/02
[52] U.S. Cl. ........................ 428/236; 428/247; 428/253; 428/255; 428/256
[58] Field of Search ................................. 428/236, 247, 428/253, 255, 256

[56] References Cited

U.S. PATENT DOCUMENTS

| | | |
|---|---|---|
| 3,288,175 | 1/1966 | Valko ........................................ 139/425 |
| 4,122,227 | 10/1978 | Dean ........................................ 428/197 |
| 4,138,519 | 2/1979 | Mitchell ................................... 428/95 |
| 4,414,260 | 11/1983 | Rzepecki et al. ....................... 428/212 |
| 4,438,174 | 3/1984 | Whewell .................................. 428/247 |
| 4,546,497 | 10/1985 | Ono et al. ................................ 2/243 A |
| 4,557,968 | 12/1985 | Thornton et al. ....................... 428/229 |
| 4,664,378 | 5/1987 | Van Auken ............................. 273/61 R |
| 4,671,841 | 6/1987 | Stephens ................................. 156/292 |
| 4,702,951 | 10/1987 | Rooklyn .................................. 428/193 |
| 4,753,088 | 6/1988 | Harrison et al. ........................ 66/202 |
| 5,009,946 | 4/1991 | Hatomoto et al. ..................... 428/87 |

Primary Examiner—Christopher W. Raimund
Attorney, Agent, or Firm—Terry T. Moyer; Earle R. Marden

[57] ABSTRACT

An antistatic fabric especially useful to upholster automobile seats having a face fabric and a backing layer with an antistatic scrim fabric secured between the face fabric and the backing fabric.

10 Claims, 2 Drawing Sheets

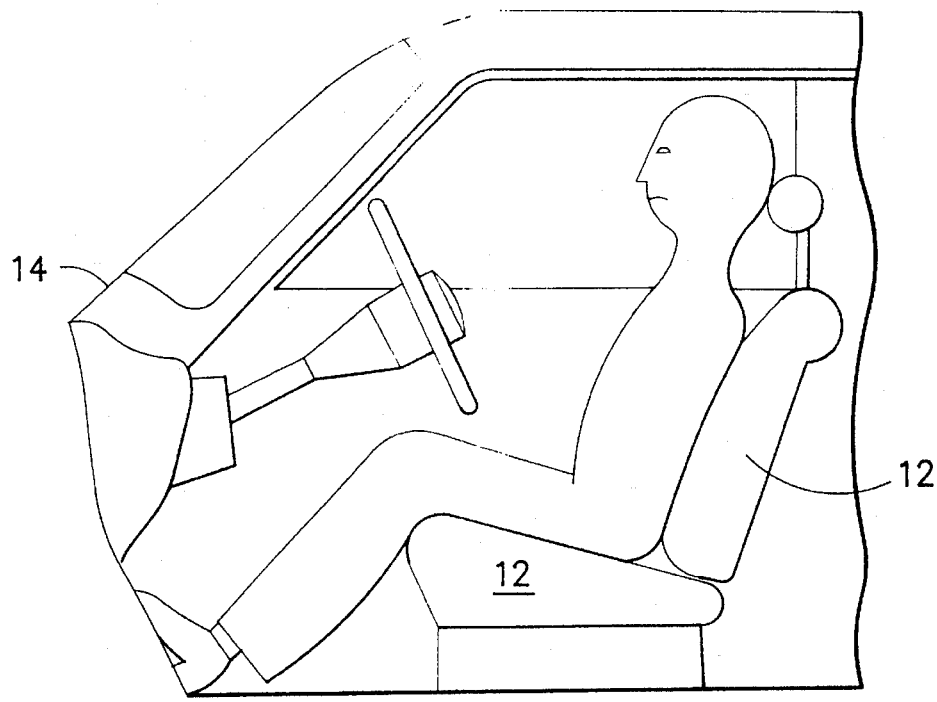
FIG. -1-
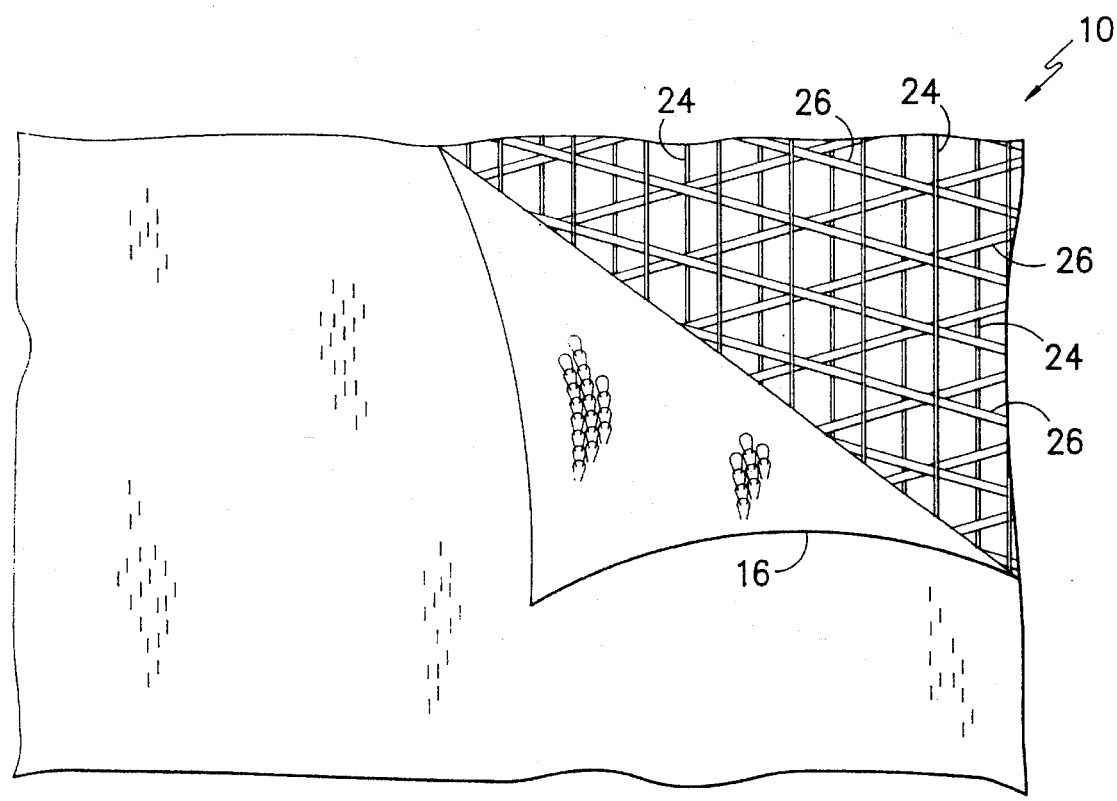
FIG. -2-

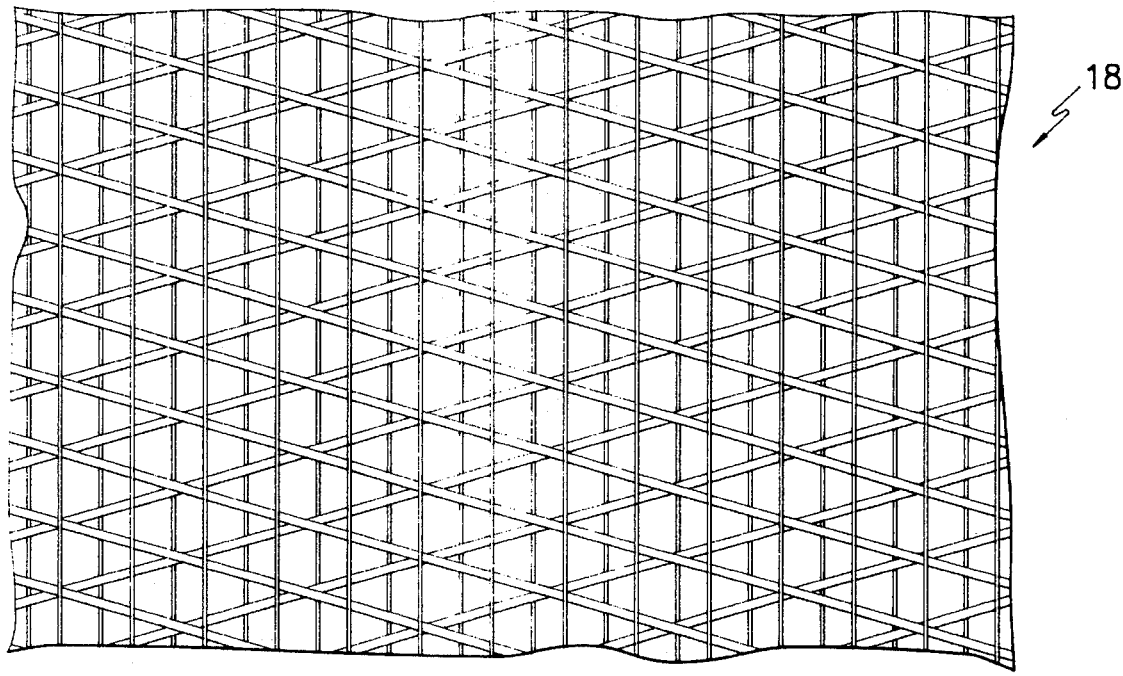
FIG. -3-
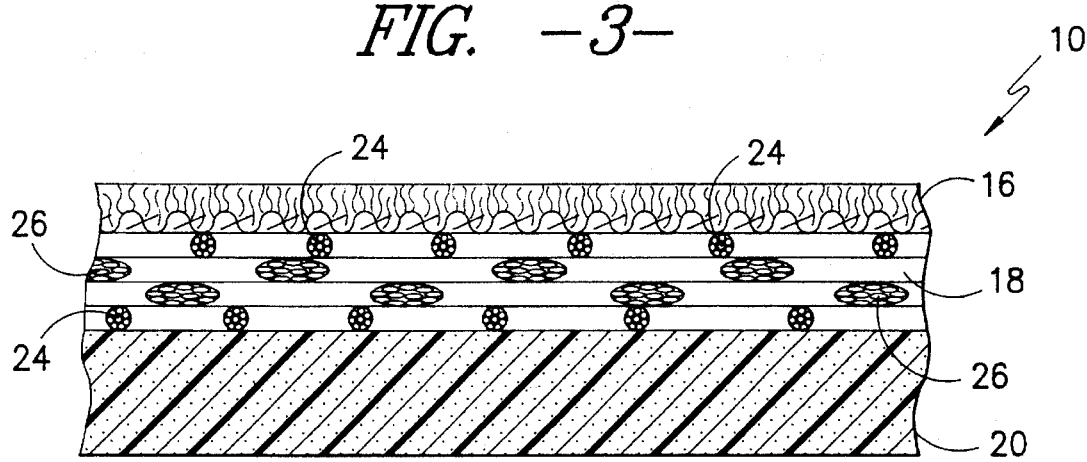
FIG. -4-
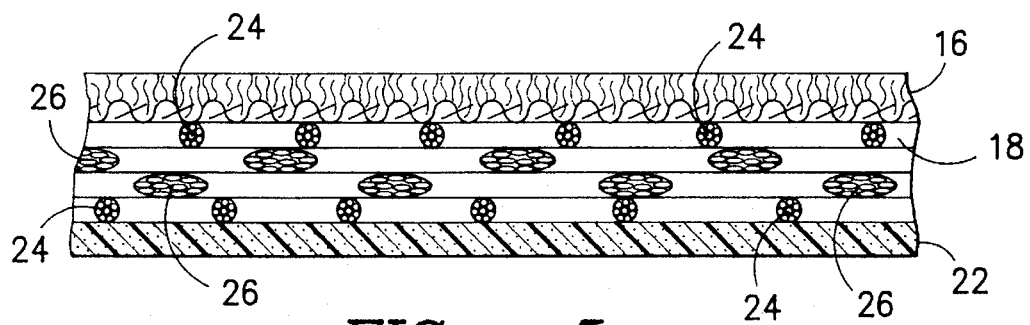
FIG. -5-

UPHOLSTERY FABRIC WITH ELECTRICALLY CONDUCTIVE BACKING

The invention relates to textile material. More particularly, the invention relates to textiles and textile materials, such as fabrics, filaments, fibers, and the like which tend to build up and maintain undesirable static charges such as automotive textile sheets and more particularly automotive upholstery sheets which have static-eliminating problems.

In general, hydrophobic fibers, such as nylon, and the like, as well as hydrophilic fibers, such as wool and cotton, at low relative humidity, tend to generate an electrical charge, that is, to build up static electricity. As a result, such fibers and textile materials made therefrom attract dust and dirt. Build-up of static electricity also causes items of apparel to cling to the body or to be attracted to other garments. Statically charged textiles can cause sparks and become highly dangerous in, for example, a place like an operating room where ether or other explosive material is generally present or around an automobile where explosive substances such as gasoline tend to accumulate.

It is well known that on rising from the driver's seat of a car after driving, one is stricken with a static shock. This shock occurs as the high static potential build up on the human body due to repeated friction against the car upholstery material, such as the driver's seat cover, is rapidly released in a burst when one contacts an electrically conductive material. This rapid, momentary release of a large static electricity is known as a spark discharge.

For an antistatic treatment of textile products, it has been known to incorporate an electrically conductive fiber in the textile construction by way of weaving or knitting. Such electrically conductive fiber serves to collect the static electricity within the textile product and discharges it as a corona discharge from its terminal ends to release the static charge from the textile product. However, the resulting corona discharge (static elimination) effect is not sufficient enough to render the product fully suitable for use as a car upholstery material. Furthermore, the static accumulating (capacitance) effect of the conductive fiber itself is also very low. Therefore, a car seat covered with such a textile product is hardly expected to eliminate the static electricity of a human body charged to a high potential through the grounding.

It is therefore an object of the invention to provide an electrically conductive fabric to eliminate the build-up of a static charge especially when used as an upholstery fabric in automobiles.

Other objects and advantages of the invention will become readily apparent as the specification proceeds to describe the invention with reference to the accompanying drawings, in which:

FIG. 1 is a schematic representation of an automobile where the new and novel fabric is used to cover the front seat thereof;

FIG. 2 is a blown-up view of the new fabric used on the seat of FIG. 1 with a portion of the face fabric rolled back;

FIG. 3 is a top view of the scrim fabric used as the antistatic layer of the fabric shown in FIG. 2 for the seat shown in FIG. 1;

FIG. 4 is a cross-section view of the fabric of FIG. 2; and

FIG. 5 is a cross-section view of a modified fabric.

In general the invention is directed to an antistatic fabric for any use in which the fabric would be exposed to a potentially explosive situation but, preferably, the disclosed fabric 10 will be used as an upholstery fabric especially for a seat 12 in an automobile as depicted in FIG. 1. The fabric 10 will be used in the exposed position where a static charge is generated such as the top fabric of an automobile seat where the driver slides thereacross to create a static charge. Other layers of material may be attached to the fabric 10 on the underside thereof to provide for comfort, etc.

The fabric 10 basically consists of a face fabric 16 which can be woven, knit, nonwoven, etc.; an intermediate electrically conductive scrim fabric 18 and a backing fabric such as a polyurethane foam 20 or film 22.

In the preferred form of the invention, the fabric 10 is employed as an upholstery fabric for an automobile seat 12. The face fabric 16 is a polyester knit fabric knit on a double needle bar Raschel knitting machine using six bars. The face yarns, knit on two bars, are 150 denier, 34 filament polyester while the ground structure is knit on four bars with the yarns on two of the bars being two ply, 150 denier, 34 filament polyester while the yarn in the other two bars is the same as the yarn for the face of the fabric. The two ply yarn includes carbon loaded fibers to enhance the antistatic characteristics of the face fabric.

The intermediate electrically conductive fabric scrim fabric 18 is preferably a triaxially wound polyester nonwoven but could be any other open construction type fabric such as woven, knit or non-woven nylon or other synthetic fabric which allows the backing fabrics to adheres to the back of the face fabric.

As described above, the preferred scrim fabric 18 is a triaxially wound fabric having 150 denier, 34 filament solution dyed, cold drawn polyester warp yarns 24 and triaxially wound textured 150 denier, 34 filament fill yarns 26. The fabric 18 is generally formed in a manner generally disclosed in U.S. Pat. Nos. 3,427,511 or 4,242,779 with the warp yarns 24 alternating between being on top of the fill yarns 26 and being on the bottom of the fill yarns 26. Before the scrim fabric 18 is formed the warp and/or the fill yarns are made electrically conductive by contacting the desired yarns under agitation conditions with an aqueous solution of a pyrrole as disclosed in U.S. Pat. No. 4,830,096. This is the preferred method to provide electrical conductivity but other methods such as using conduction fibers in the scrim fabrication can be used within the scope of the invention.

In the form of the invention shown in FIGS. 2–4 a polyurethane foam, treated with flame retardants and having a density of about 1.9 pounds/foot$^3$ and a thickness of 3 mils is flame laminated to the back of the face fabric 16 through the openings in the electrically conductive scrim fabric 18. Flame lamination is a commercially viable system to soften the surface of the foam 20 to allow it to flow through the scrim fabric 18 and adhere to the face fabric. Other foams such as polyester or polystyrene, etc. can be used.

As mentioned above the warp and/or fill yarns are treated to provide electrical conductivity but it is within the scope of the invention to treat the fabric after formations to provide electrical conductivity thereto. Also, the surface or back of the face fabric can be treated with an antistatic compound such as quanternerary compounds or polyethoxylates but as pointed out, this treatment is not permanent while the treated scrim fabric 18 will provide permanent antistatic characteristics.

The modification shown in FIG. 5 involves substituting a polyurethane film or other suitable films such as polyester or polyamide for the foam of FIGS. 1–4 which is laminated to the face fabric by heating same and then running the fabric 10 through pressure rolls to bring the film 22 into intimate contact with the back of the face fabric 16 through the scrim fabric 18 and allowing it to cool.

As indicated previously, the fabric 10 can be used as the top upholstery fabric for a car seat 12 because it is readily moldable and at the same time provides permanent resistance to the build-up a static charge cause by surface friction thereagainst by the occupant of the car.

Although the preferred embodiments of the invention have been described, it is contemplated that any charges may be made whether the scope of the invention without departing from the spirit thereof and it is, therefore, desired that the invention be limited only by the claims.

We claim:

1. A composite fabric especially useful as an upholstery fabric comprising: a face fabric, a foam backing material and an electrically conductive scrim fabric secured between the face fabric and the backing material, said scrim fabric being a triaxially wound non-woven scrim.

2. The fabric of claim 1 wherein said foam backing material is a urethane.

3. A composite fabric especially useful as an upholstery fabric comprising: a face fabric, a foam backing material and an electrically conductive scrim fabric secured between the face fabric and the backing material, said scrim fabric being a non-woven scrim.

4. The fabric of claim 3 wherein said foam backing material is a urethane.

5. A car seat backing having an upholstery fabric thereon, said upholstery fabric having substantial permanent electrical conductivity and comprising: a face fabric, an electrically conductive scrim fabric abutting and adjacent thereto and a foam backing material on the side of the scrim fabric away from the face fabric said foam backing material adhered to said face fabric through said scrim fabric.

6. The fabric of claim 5 wherein said backing material is a urethane foam.

7. The fabric of claim 5 wherein said scrim fabric is a triaxially wound non-woven fabric.

8. The fabric of claim 7 wherein said backing material is a urethane foam.

9. A car seat backing having an upholstery fabric thereon, said upholstery fabric having substantial permanent electrical conductivity and comprising: a face fabric, an electrically conductive triaxially wound non-woven scrim fabric abutting and adjacent thereto and a backing material of polyurethane film on the side of the scrim fabric away from the face fabric said backing material adhered to said face fabric through said scrim fabric.

10. A car seat backing having an upholstery fabric thereon, said upholstery fabric having substantial permanent electrical conductivity and comprising: a face fabric, an electrically conductive triaxially wound non-woven scrim fabric abutting and adjacent thereto and a backing material on the side of the scrim fabric away from the face fabric adhered to said face fabric, said backing material through said scrim fabric, said face fabric containing carbon loaded fibers and an anti-static compound.

* * * * *